United States Patent [19]
Johnson et al.

[11] Patent Number: 4,650,173
[45] Date of Patent: Mar. 17, 1987

[54] METHOD OF OPERATING A DIAPER PRODUCING MACHINE AND APPARATUS

[75] Inventors: Gary E. Johnson; Andrew M. Van Egeren, both of Green Bay; James F. Campbell, New Franken; Harvey J. Spencer, Green Bay, all of Wis.

[73] Assignee: Paper Converting Machine Co., Green Bay, Wis.

[21] Appl. No.: 734,896

[22] Filed: May 16, 1985

Related U.S. Application Data

[63] Continuation-in-part of Ser. No. 630,647, Jul. 13, 1984, Pat. No. 4,519,596.

[51] Int. Cl.⁴ .............................................. B42C 1/00
[52] U.S. Cl. ........................................ 270/45; 493/12; 493/416; 493/437; 493/454
[58] Field of Search .......................... 270/58, 49, 50, 32, 270/45; 493/405, 412, 416–417, 419, 422, 425, 429, 431, 436, 437, 454, 23, 27, 29, 3, 842, 16, 12, 25, 28, 35, 36, 424, 937

[56] References Cited

U.S. PATENT DOCUMENTS

| | | | |
|---|---|---|---|
| 2,072,937 | 3/1937 | Beattie | 493/416 |
| 3,003,760 | 10/1961 | Scheu, Jr. et al. | 493/28 |
| 3,190,640 | 6/1965 | Sjostrom | 493/422 |
| 3,339,914 | 9/1967 | Grantham | 493/23 |
| 3,363,897 | 1/1968 | Northern et al. | 493/23 |
| 3,475,018 | 10/1969 | Mattka | 493/417 X |
| 3,692,303 | 9/1972 | Grantham | 493/23 |
| 3,790,157 | 2/1974 | Crawford et al. | 493/23 |
| 4,053,150 | 10/1977 | Lane | 493/417 |
| 4,085,928 | 4/1978 | Sussman | 493/405 |
| 4,519,596 | 5/1985 | Johnson et al. | 493/416 |

FOREIGN PATENT DOCUMENTS

| | | | |
|---|---|---|---|
| 2323433 | 11/1974 | Fed. Rep. of Germany | 493/419 |
| 612467 | 11/1948 | United Kingdom | 493/416 |
| 763169 | 12/1956 | United Kingdom | 493/419 |
| 1167327 | 10/1969 | United Kingdom | 493/431 |

*Primary Examiner*—E. H. Eickholt
*Attorney, Agent, or Firm*—Tilton, Fallon, Lungmus & Chestnut

[57] ABSTRACT

A method and apparatus for operating a diaper-producing machine where a series of unfolded diapers are advanced along a path containing a plurality of stackers each having a folding blade, the apparatus having means for periodically altering the movement of one blade to permit diaper movement past that stacker to a subsequent one, thereby continuing stacking while a previously completed stack is removed.

12 Claims, 5 Drawing Figures

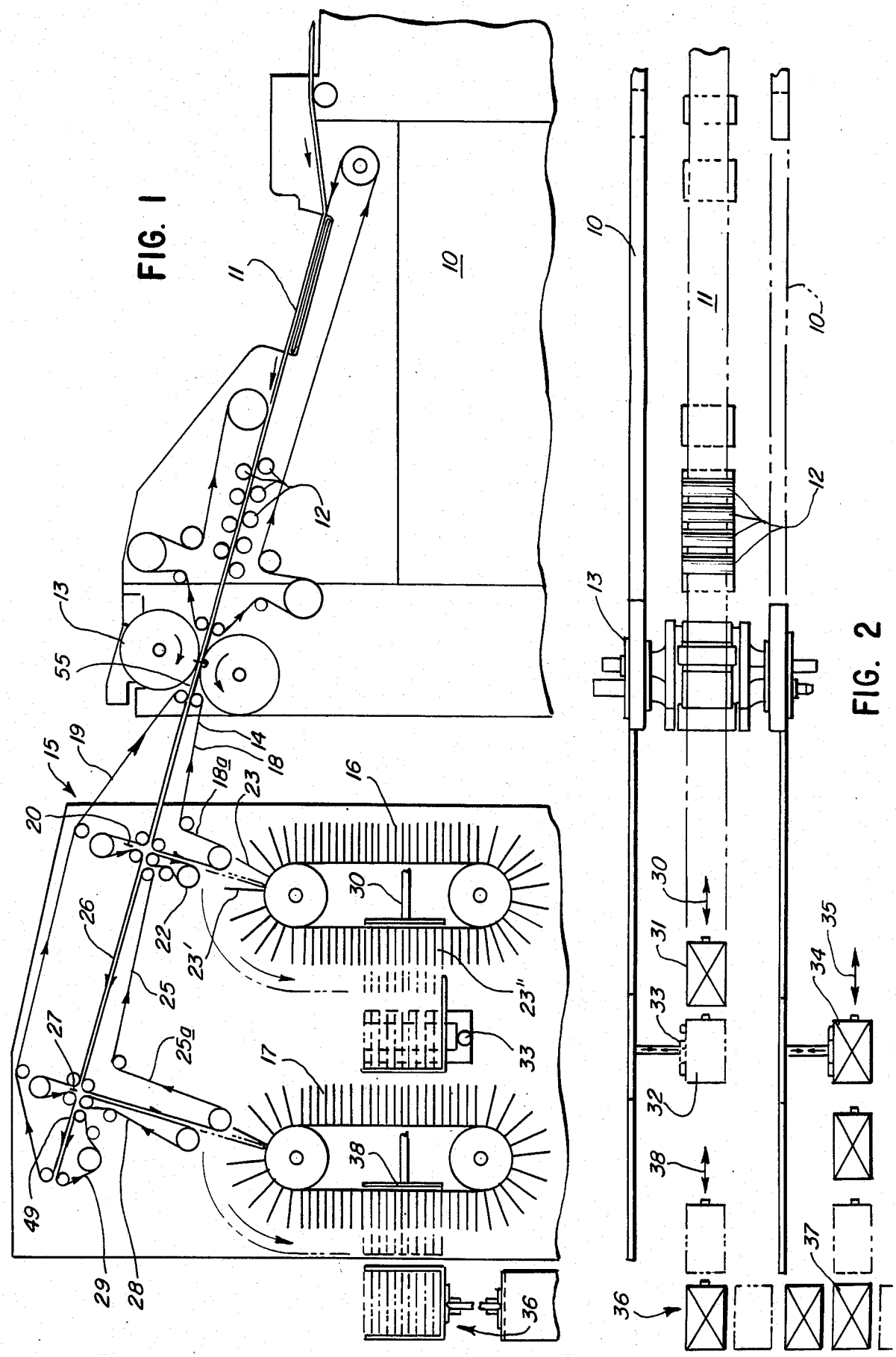

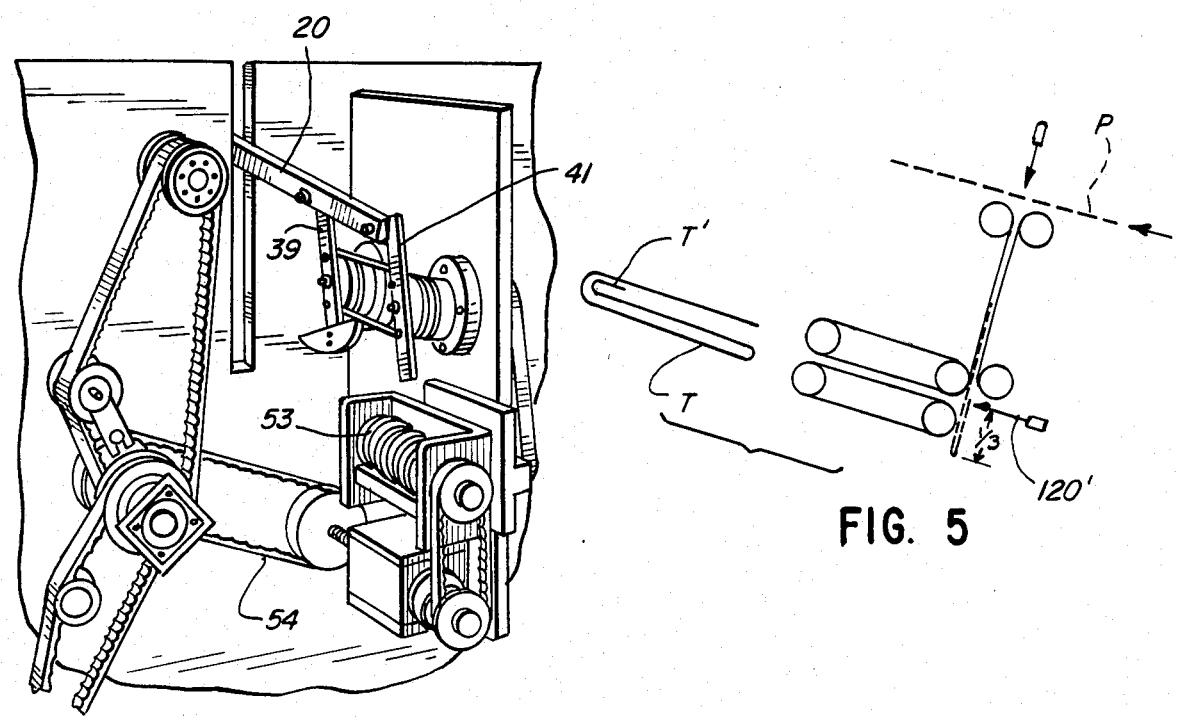
FIG. 3
FIG. 5
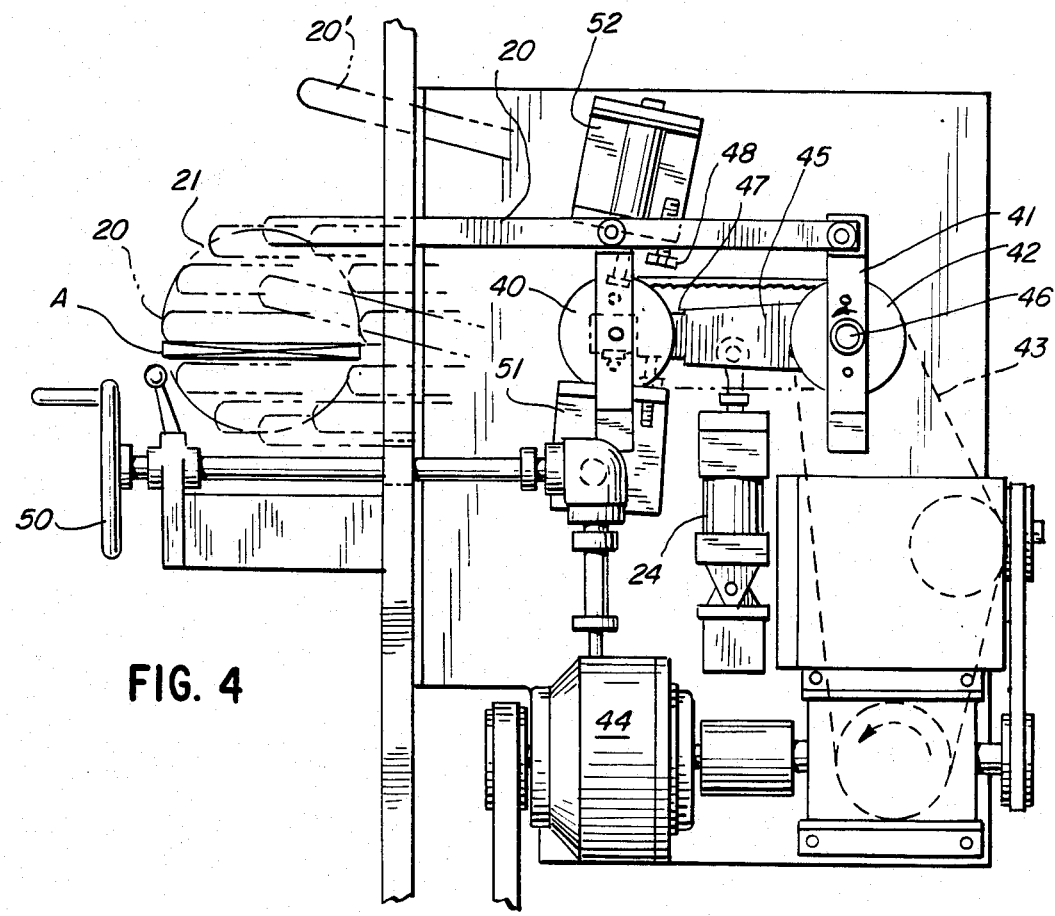
FIG. 4

METHOD OF OPERATING A DIAPER PRODUCING MACHINE AND APPARATUS

This application is a continuation-in-part under Public Law 98-622 of Gary E. Johnson and Andrew E. Van Egeren, U.S. Ser. No. 630,647, filed July 13, 1984, now U.S. Pat. No. 4,519,596.

BACKGROUND AND SUMMARY OF INVENTION

This invention relates to a method of operating a diaper-producing machine and apparatus and, more particularly, to method and apparatus which make possible the development of "short-count" stacks of diapers at high speed.

Historically, diapers have been folded and introduced into vane-type stackers, "see for example, U.S. Pat. Nos. 4,056,919 and 4,325,475. Vane-type stackers per se are quite well known—see, for example, U.S. Pat. No. 2,324,930.

Disposable diaper-producing machines have become available at higher and higher speeds which have been somewhat limited by the time required to remove diaper stacks from the stackers. This has been addresssed in the U.S. Pat. Nos. 4,056,919 and 4,325,475 and also is the objective of co-owned application of James F. Campbell, U.S. Ser. No. 506,508, filed June 21, 1983. However, none of these prior approaches was able to deal with the requirement of a "short count". Conventionally, diapers were packed 12 to a box so the time for removal of a dozen diapers at one time from the stacker could generally be tolerated. Now, however, disposable diaper manufacturers desire to put out much smaller units, 5 or 6 diapers per stack and even as low as 2 diapers per stack. Stacks may be packaged 2 or more stacks/package. The approach to dealing with this problem has been to divide the lineal stream of diapers issuing from the diaper producing machine into a plurality of parallel paths. This requires quite complex machinery with the attendant risk of unforeseen breakdown and therefore interruption of the entire line.

With the invention of the Method and Apparatus for Folding Diapers of Johnson and Van Egeren, U.S. Ser. No. 630,647, filed July 13, 1984, now U.S. Pat. No. 4,519,596, it has become possible to arrange stackers in lineal fashion at spaced positions along the diaper discharge path. More particularly, the disarmable blade feature of Johnson and Van Egeren makes possible the unloading of one stacker while one or more other stackers are being loaded—so as to remove all time constraints.

Other objects and advantages of the invention may be seen in the details of construction and operation set forth in the ensuing specification.

The invention is described in conjunction wth the accompanying drawing, in which FIG. 1 is a fragmentary elevational view—essentially schematic—of apparatus employed in the practice of the invention;

FIG. 2 is a plan view of the apparatus of FIG. 1;

FIG. 3 is a fragmentary perspective view of the folding blade apparatus portion of FIGS. 1 and 2;

FIG. 4 is an end elevational view of the apparatus portion seen in FIG. 3; and

FIG. 5 is a schematic view of a modified form of the invention.

DETAILED DESCRIPTION

Referring first to FIG. 1 and to the right hand portion thereof, the discharge end of a diaper-making machine is depicted essentially schematically. The extreme right hand portion of the machine can include a longitudinal folder 11 which longitudinally folds the continuous stream of diapers to approximately one-third of its width. For a description of what typically occurs upstream, see co-owned U.S. Pat. No. 4,417,935.

The continuous longitudinally folded web product from 11 passes through compression rolls 12 and a transverse cutoff 13 wherein individual diapers are achieved and delivered to a conveyor 14 for advancement into a stacking assembly generally designated 15. The stacking assembly 15 includes, in the illustration given, two stackers 16 and 17. It will be appreciated that any number can be employed, depending upon the "shortness" of the count. Further, the stackers may be disposed for rotation about vertical axes as contrasted to the horizontal axes illustrated.

As a diaper is advanced by the conveyor 14, more particularly, the lower belt system 18 and the upper belt system 19, it comes into alignment with the folding blade 20 associated with the first stacker 16. This can be seen in greater detail in FIGS. 3 and 4 which reproduce the structure described in greater detail in the above-identified application of Johnson and Van Egeren.

The blade 20 moves in an orbit 21—see FIG. 4—which causes the blade 20 to fold the diaper A and force it into the nip defined in part by a vertically-extending section 18a of the lower belt system 18 and a cooperating vertically-extending belt system 22. This causes the diaper to be introduced between adjacent vanes 23 and 23' of the first stacker 16.

The orbital, folding action of the blade 20 continues until a suitable number of diapers have been loaded into the stacker 16. For this purpose, the stacker 16 is indexed by suitable mechanisms such as that described in conjunction with the above-identified U.S. Pat. No. 4,325,475.

When a suitable number of diapers have been loaded into the stacker 16—reaching the position designated 23'', the orbit of the blade 20 is displaced upwardly under the influence of the cylinder and piston rod unit 24—see the central part of FIG. 4—resulting in the orbit being upwardly displaced as designated by the location of the folding blade designated 20'.

Thereupon, the diapers continue past the folding blade 20 under the influence of a second lower belt system 25 and the lower run 26 of the upper belt system 19 until diapers come into alignment with the second stacker folding blade 27. The second folding blade 27 functions similarly to the first folding blade 20 and forces folded diapers into the nip defined in part by a vertically-extending portion 25a of the second lower belt system 25 and a cooperating vertically-extending belt system 28.

In normal operation, the second folding blade 27 orbits continuously in a lower (folding) orbit or in a displaced (non-folding) orbit. In the displaced orbit, blade 27 does not intersect the path of diaper transport and thus cannot cause folding of the diaper. The same is true of folding blade 20 associated with first stacker 16. Folding blades 20 and 27 are only displaced to the upper (non-folding) orbit when it is intended that diapers are to be passed through the blade folding station without being folded—for example, cull or sub-quality diapers.

Whenever a defective diaper passes the second folding blade 27, it is conveyed to a disposal position by a third lower belt system 29 and the lower run 26 of the upper belt system 19.

When the diapers are all acceptable, and the two stackers 16 and 17 are sufficient to handle the output, first one stacker is loaded and then the other. While the second stacker is being loaded, the first stacker is unloaded as by the pushing device 30.

The pusher device 30 moves a stack of diapers—ten as illustrated—from a position 31 (see FIG. 2) in the stacker to a horizontally displaced position 32. Thereafter, a second pusher device 33 moves the stack of diapers to the position 34 and a third pusher device 35 moves the stacks sequentially and incrementally into a takeaway conveyor generally designated 36 and at the position 37.

Meanwhile, the pusher 38 associated with the second stacker 17 also sequentially and incrementally moves diaper stacks into alternate buckets of the takeaway conveyor 36.

It will be appreciated that only two stackers and the pushing device arrangements associated therewith have been illustrated for ease and clarity of illustration but any number can be used within the spirit and scope of the invention.

Blade Tucker Control Mechanism

The ensuing description is rather summary in nature inasmuch as greater details of this mechanism can be found in the above-identified Johnson and Van Egeren Application Ser. No. 630,647, filed July 13, 1984, now U.S. Pat. No. 4,519,596.

Referring now to FIGS. 3 and 4, the blade 20 is seen to be pivotally mounted on a first arm 39 which is eccentrically attached to and rotated with an idling timing belt pulley 40. A second arm 41 is eccentrically attached to and rotatable with a driven timing belt pulley 42—this system constituting a parallel motion orbiting mechanism. The numeral 43 designates a belt traveling between the two pulleys and which delivers rotational power thereto from a phasing box 44 to which rotational input is provided by means (not shown).

When it is desired to disarm a particular folding blade 20, 27, etc., the associated lift cylinder 24 is energized which pivots link 45 about shaft 46 until the machined flat 47 contacts stop screw 48. This particular operation is performed either when it is desired to shift the loading of diapers from one stacker to another or, when a defective diaper appears in the stream and is not to be stacked at all. In such a case, both folding blades 20 and 27 are disarmed whereby the diaper then passes beyond alignment with the second folding blade 27 and into the nip 49 defined by the third lower belt system 29 and the lower run 26 of the upper belt system 19 seen to the extreme right in FIG. 1. The belt system 29 and lower run 26 are arranged to conduct the defective diaper to a suitable storage area away from the stackers 16, 17.

The phasing box 44 constitutes a means to adjustably phase the blade motion with the diapers so that the blade at its maximum velocity—maximum extension to the left—contacts the diaper halfway along its length. This is under the control of the operator by suitable hand wheel means 50.

As the orbit or disarming of the folding blade 20, 27, etc. is brought about, the link 45 is stabilized in its rapid motion—several hundred blade strokes per minute—by virtue of shock absorbers 51 and 52 provided at both the top and bottom of the stroke.

Omitted from the showing in FIG. 3 for clarity of presentation is the orbit shifting mechanism including the lift cylinder 24, link 45 and shock absorbers 51, 52. However, seen in FIG. 3 is a timing switch 53 which is used to phase the electrical impulse triggering the air cylinder 24 which, in turn, displaces the orbit of the folding or tucker blade 20. Still referring to FIG. 3, the numeral 54 designates a belt traveling between two pulleys, one of which is connected to a hand wheel shaft for regulating the phasing of the blade movement.

Culling is advantageously achieved by suitable sensing means as at 55 in FIG. 1 to ascertain whether the diaper is complete and acceptable, viz., equipped with suitable tape tabs, rectangular in nature, etc. A special advantage of the blade folder is the ability to switch from a folding to a non-folding mode while the folder continues to run at top speed. By displacing the orbit of the continuously running blade, it is deactivated from a folding to a nonfolding mode, but the very high inertia forces involved in abrupt stoppage are avoided, and this accounts for the unique ability of the folder to be deactivated on command at high speeds. Thus, it is noted that the folding blades 20 and 27 are operated continuously and are switched from the folding to non-folding mode and vice versa by moving the pivotable arm supporting the folding means.

In the example given, two stacking devices 16 and 17 are described. The number of diapers "in-transit" between two adjacent stackers is a function of the distance between stackers. It will be recognized that as the "in-transit" diapers become a different proportion of the total number of diapers in a given stack, actuation or switching of the blade folder 20 or 27 from a folding to non-folding mode or vice versa must be phased differently to account for a different proportion of in-transit diapers. In essence, when switching from stacker 16 to 17, the effect of blade folder 27 can be delayed relative to the first stacker, and when switching from stacker 17 to 16, the action and effect of blade folder 27 must likewise be delayed to fold the last few diapers, and thus, complete a stack before switching to the first stacker.

The invention is capable of advantageous modification—by making the tri-folded diaper T of FIG. 5. By phasing the second folding blade 120', a fold-back portion T' can be produced. In FIG. 5, the diaper path P is not lineal but includes two legs for tri-folding.

While in the foregoing specification a detailed description of an embodiment of the invention has been set down for the purpose of illustration, many variations in the details hereingiven may be made by those skilled in the art without departing from the spirit and scope of the invention.

We claim:

1. A method for operating a diaper-producing machine comprising advancing a series of unfolded diapers along a first path, moving a tucker blade for each diaper through said path to fold the diaper and deliver the now-folded diaper to a second path, and selectively displacing the movement of said tucker blade out of said first path, said tucker blade being orbited through said first path.

2. A method of claim 1 in which said tucker blade orbits in the range of about 500 to about 600 times per minute.

3. The method of claim 2 in which said tucker blade is cushioned when the orbit thereof is displaced.

4. A method for operating a diaper-producing machine comprising advancing a series of unfolded diapers along a path toward a plurality of stackers in said path, each stacker having a folding blade associated therewith and movable generally perpendicularly to said path and adapted to foldably introduce a diaper into its associated stacker, periodically altering the movement of one of said stacker blades to permit continued advancement of a portion of said series past the stacker associated therewith and toward a subsequent stacker while substantially simultaneously therewith, removing a stack of diapers from said one stacker.

5. The method of claim 4 in which while said stack is being removed from said one stacker, the folding blade associated with another of said stackers is introducing diapers thereinto.

6. The method of claim 4 in which all of said folding blades are serially disabled from introducing diapers into their associated stackers whereby a defective diaper is advanced in said path beyond said plurality of stackers for culling.

7. A method for operating a diaper-producing machine comprising advancing a series of unfolded diapers along a generally lineal path toward first and second stackers aligned in said path, each stacker having a folding blade associated therewith with each blade being movable generally perpendicularly to said path and adapted to foldably introduce a diaper into its associated stacker, altering the movement of the first stacker blade to permit continued advancement of a portion of said series removing a multiple diaper stack from said first stacker during said first stacker folding blade movement altering, moving said second stacker folding blade relative to said diaper series portion to create a multiple diaper stack in said second stacker, and removing a multiple diaper stack from said second stacker during the time said first stacker folding blade is introducing diapers into said first stacker.

8. The method of claim 7 in which the movement of each blade is selectively alterable to permit a defective diaper to continue to be advanced in said path beyond said second stacker.

9. The method of claim 8 in which each stacker is indexed in synchronism with the movement of its associated folding blade incident to introducing a diaper thereinto, and halting each stacker indexing incident to the advance of a defective diaper under folding blade of each such stacker.

10. The method of claim 10 in which each stacker is indexed in synchronism with the movement of its associated folding blade, incident to introducing a diaper thereinto, and periodically halting the indexing of each stacker to remove a multiple diaper stack therefrom.

11. Apparatus for operating a diaper producing machine comprising a frame, means on said frame for advancing a series of unfolded diapers along a path toward a plurality of stackers in said path, each stacker having a folding blade associated therewith and movable generally perpendicularly to said path and adapted to foldably introduce a diaper into its associated stacker, and means on said frame for periodically altering the movement of one of said blades to permit continued movement of a portion of said series past the stacker associated therewith and toward a subsequent stacker while substantially simultaneously therewith removing a stack of diapers from said one stacker.

12. The apparatus of claim 11 in which each of said stackers is equipped with pusher means for advancing stacks of diapers sequentially, incrementally toward and onto a takeaway conveyor.

* * * * *